(12) United States Patent
Jones

(10) Patent No.: US 6,367,958 B1
(45) Date of Patent: Apr. 9, 2002

(54) THREE DIMENSIONAL DIMMER

(75) Inventor: Eric M. Jones, Southbridge, MA (US)

(73) Assignee: Karl Storz Endovision, Charlton, MA (US)

(*) Notice: Subject to any disclaimer, the term of this patent is extended or adjusted under 35 U.S.C. 154(b) by 0 days.

(21) Appl. No.: 09/537,158

(22) Filed: Mar. 29, 2000

(51) Int. Cl.[7] .................................................. F21V 7/04
(52) U.S. Cl. ........................................ 362/552; 359/892
(58) Field of Search ................................ 362/552, 551, 362/554, 556, 572, 574, 322, 311, 275, 257, 321, 323, 324, 539, 512, 513; 359/892, 893, 291, 234, 888, 889

(56) References Cited

U.S. PATENT DOCUMENTS

| 4,233,650 | A | | 11/1980 | Hagner et al. |
| 4,425,599 | A | | 1/1984 | Rieder et al. |
| 5,006,965 | A | * | 4/1991 | Jones ........................ 362/277 |
| 5,207,494 | A | | 5/1993 | Jones |
| 5,488,509 | A | | 1/1996 | Takahaski et al. |
| 5,513,286 | A | | 4/1996 | Easley |
| 5,642,456 | A | * | 6/1997 | Baker et al. ................ 385/140 |
| 5,803,900 | A | | 9/1998 | Matsumoto et al. |

* cited by examiner

Primary Examiner—Sandra O'Shea
Assistant Examiner—Bao Truong
(74) Attorney, Agent, or Firm—St. Onge Steward Johnston & Reens LLC

(57) ABSTRACT

An endoscopic device includes a dimming assembly having an array of segments which is successively insertable into a path of a light beam. The segments have outlines of different geometric shapes defining a configuration of a transmission region depending upon an angular position of the shaft.

23 Claims, 7 Drawing Sheets

PRIOR ART
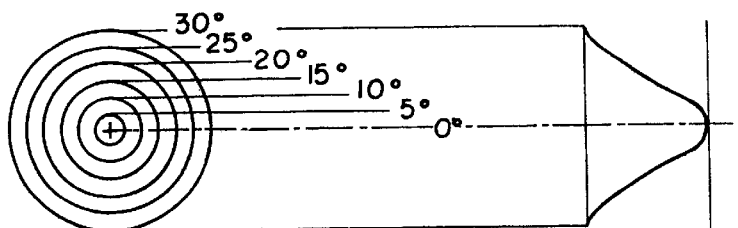
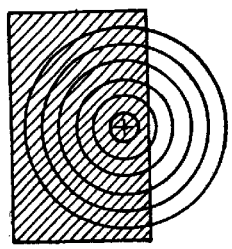 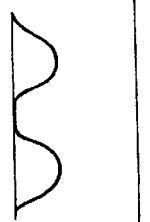
FIG. 1A
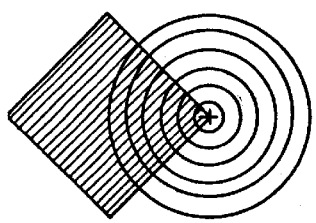 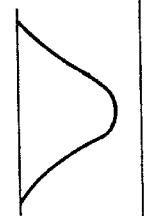
FIG. 1B
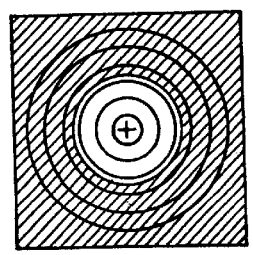 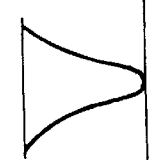
FIG. 1C
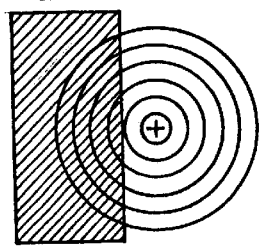 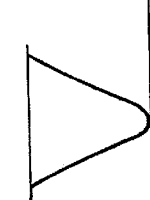
FIG. 1D

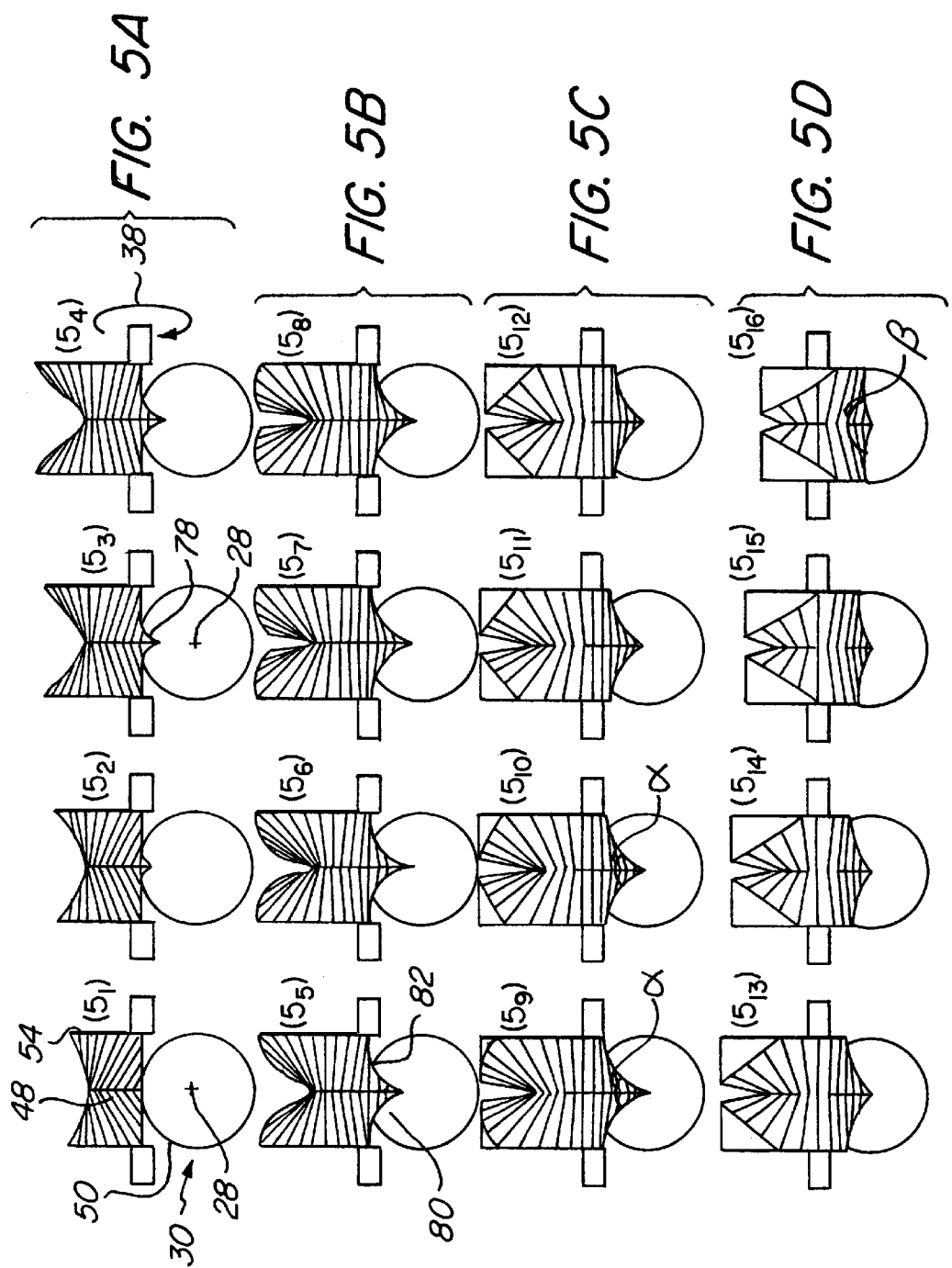

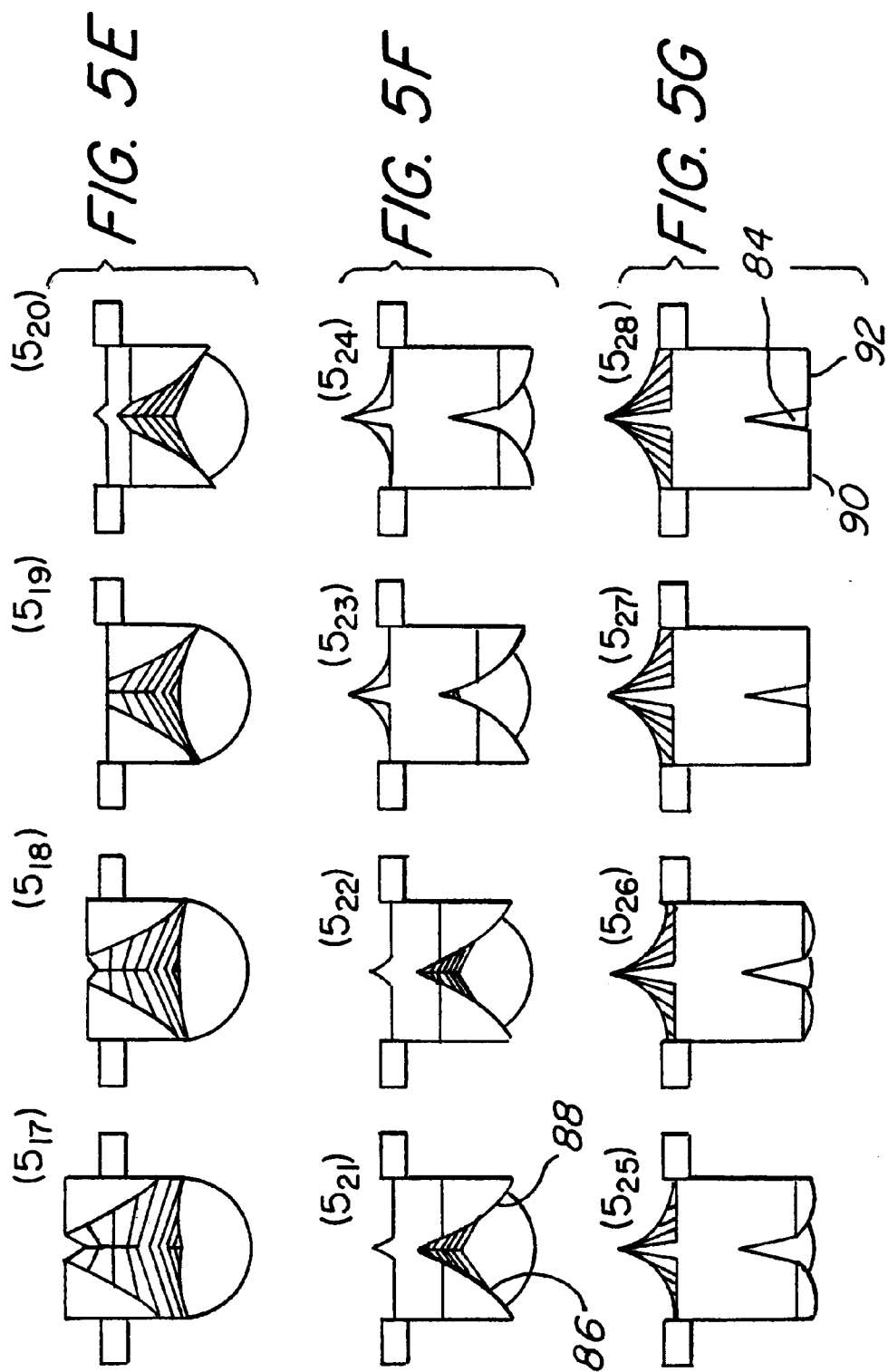

THREE DIMENSIONAL DIMMER

FIELD OF THE INVENTION

The invention relates to a device for adjusting light intensity provided by a lamp to a fiberoptic light transmission system. Particularly, the invention relates to a dimmer controllably intercepting a beam of light to regulate light flux impinging on the entrance of a fiberoptic conductor. More particular, the invention relates to a three dimensional dimmer controllably adjusting light which is transmitted through it to a fiberoptic conductor from a light source used for illuminating a bodily cavity during an endoscopic surgical operation.

BACKGROUND OF THE INVENTION

Fiberoptic systems used in endoscopic surgery for illuminating an interior of a cavity have become practically indispensable in various surgical procedures. One of the primary reasons for such widespread use of a fiberoptic system is its flexibility allowing a surgeon to illuminate and, thus, to observe inside regions of the bodily cavity that are not easily accessible. Typically, a fiberoptic conductor includes a multiplicity of light conducting fibers, e.g. glass fibers, in the form of a bundle or strand, and extends between an entrance plane and an exit plane which is placed near the site that is to be illuminated.

Fiberoptic systems typically utilize a high intensity lamp as a light source in endoscopic procedures. Too high or too low an intensity of light can detrimentally affect the vision of a surgeon or imaging device. As a consequence, control of the luminous intensity at the exit plane of a fiber conductor has gained a particular significance in the endoscopic surgical procedures. Particularly, the ability to adjust intensity of the light without its distortion becomes critically important.

Numerous attempts have been made to vary the luminous intensity or light-flux from the lamp's output. Typically, these attempts have involved changing the feeding current or voltage or phase of the light source. This control, however, is typically accompanied with changes in the color temperature of the light source and, thus, the color of the illuminated object. The latter is particularly disadvantageous if the image is to be photographed or transmitted or recorded by video techniques, as well as making tissue color determination essential in disease diagnosis, difficult or impossible.

To solve the color change problem, attempts have been redirected to influence illumination of a cavity by introducing a mechanical dimming device or dimmer which is arranged in the optical path between a light source and the entrance plane of a fiberoptic conductor. Utilization of mechanical control devices basically obviates the necessity for interference with the power supply of the light source and eliminates the color temperature change of the emitted light.

Typically, a dimmer is a two-dimensional disk-shaped element which is controllably displaceable along the optical path to alter the light flux impinging upon the entrance plane of a fiber conductor. Displacement, which can be rotational and/or linear, leads to dimming the intensity of light provided to an optical fiber conductor by covering at least a portion of its entrance plane.

The conventional dimmer assembly suffers, however, from the problem that the control of the incident luminous flux causes a change in the course of passage of illuminating light entering the fiber conductor. This, in turn, leads to considerable variation in the light-distribution characteristics of illuminating light emanating from the conductor.

Still another problem characteristic of the conventional mechanical dimmer is that it may be impossible to avoid a change of the course of passage of illuminating light caused by a change in the luminous flux of light which enters a fiberoptic conductor. Therefore, when the luminous flux of illuminating light changes to a considerable extent upon entering a fiber conductor, a distinct change occurs in the light distribution and spectral characteristics of light at its exit plane.

Several attempts have been made to overcome these problems. Typically, a circular disk is placed perpendicular to the light axis and between a lamp and a fiber conductor. The disk may be perforated and have different arrangements of perforations designed to gradually block the light upon the disk's displacement. Basically, this type of the mechanical dimmer is directed at a change in the aperture and has been favorably accepted in the endoscopic medical field.

U.S. Pat. No. 5,006,965 to Jones discloses a disk including an outer peripheral imperforate band and an inner perforate band which is provided with differently sized and variably spaced apart slots. The disk further has a part of its active length open so as when this open portion is in the path of the light beam, 100% of the latter is transmitted to an optical conductor. It is clear that the outer beam stops 50% of the beam, whereas the slots of the inner beam control the rest of the beam.

One of the problems this structure may pose is that a small amount of movement of the disk between its fully open and partly closed regions causes an abrupt and large change of the quantity of illuminating light. This is largely due to the fact that typically the disc may be quite large in proportion to the optical beam diameter.

Another problem associated with many types of planar circular dimmers including the one described above is that using such a disk may cause the outer edges of an output circle of the optical fiber to become smeared and later become dark, a phenomenon known as "ringing".

Still another problem of such structure is that a distribution of the output light is not monotonically variable throughout a substantial range of light-to-dark. Dimming the light incident on a fiberoptic light guide aperture requires that on the average all rays from all acceptance angles must be dimmed the same amount, as well described by Walter P. Siegmund (Walter P. Seigmund, *Handbook of Optics* (1978)). There are many ways to get a single perfect distribution of the output rays, however this "perfect" distribution is not monotonically variable negatively affecting illumination of a bodily cavity during an endoscopic surgical operation.

U.S. Pat. No. 4,233,650 to Hagner discloses a dimmer comprised of three diaphragms controllably displaceable with respect to one another to asymmetrically and unilaterally reduce the cross section of an entrance plane of a fiber conductor.

One of the obvious problems of this structure may be that a part of the entrance plane is always dimmed because the light beam is invariably blocked by inwardly extending vanes. In practical terms, however, a situation when a surgeon needs unhindered illumination of a cavity is quite frequent. Another problem associated with this structure is that a control mechanism regulating displacement of the three rings may be complicated. Still another problem is that the ringing phenomenon still may not be fully eradicated.

Many attempts have been made to use conventional optical diaphragms, such as an iris diaphragm. A problem common to many of these diaphragms is that they typically change the average entrance angle of the light into a fiberoptic conductor and the exit angle at its exit plane.

Referring to FIGS. 1a–1e, the results of various dimming schemes known in the prior art are shown. FIG. 1a shows the unblocked normal profile of a source of light.

FIG. 1b shows a diaphragm 12 crossing the center of the entrance plane of a fiberoptic conductor. It is clear that the light intensity is reduced all over a surgical area, and, particularly, a central region is totally dark FIG. 1c illustrates a segment of the entrance plane being blocked. This structure imposes an upper limit on the light transmission, defined by the blocked sector.

Referring to FIG. 1c, disadvantages of an iris diaphragm mentioned above become clearer. Particularly, a beam width is reduced, thereby darkening peripheral regions of an illuminated surgical area while its central region may be disproportionately illuminated.

Finally, FIG. 1d illustrates a screen occluding part of an optical beam so as the central region of a surgical area is sharply illuminated by contrast with a darkened outer ring.

What is desired, therefore, is a dimmer that produces an output beam having substantially uniform intensity without a disproportionately illuminated center and/or dark peripheral regions. A dimmer having a substantial dynamic range of adjustment of light throughput, thereby eliminating a ringing phenomenon is also desirable. Further, a dimmer providing a constant light entry without reducing the maximum light flux emitted by the light source is also desirable, as is a three dimensional dimmer that produces monotonic dimming of a fiberoptic conductor.

SUMMARY OF THE INVENTION

With a dimmer in accordance with the invention, gradual adjustment of light throughput of a fiberoptic conductor can be dynamically performed by occluding fractions of an optic beam from a light source without developing a ringing phenomenon.

This is achieved with a dimming assembly in accordance with the invention by using a three-dimensional light-transmissivity shaper (also referred to as a dimmer) positioned along an optical path of light beam and projected in into a two-dimensional entrance plane of the fiberoptic conductor. To provide gradual adjustment of light throughput of the fiberoptic conductor, a dimmer has a compound geometrical shape symmetrical with respect to a plane of symmetry of the dimmer, which extends perpendicular to its axis of rotation. The rotation axis extends in the same plane as an optical axis of the light beam but perpendicular thereto.

In accordance with a cardinal concept of the invention, the dimmer is a solid body having an aspheric shape meaning "shape with horns" or a wedge shape, if viewed along an optical axis, which is perpendicular to an axis of rotation of the body. The solid body is also mirror symmetrical about a plane of symmetry perpendicular to the axis of rotation and has substantially a semi-circular shape going from convex to concave, if viewed along the axis of rotation. Thus, the body may have an unlimited number of successive wedge-shaped axial planes terminating in the plane of symmetry. Therefore, each of the radial planes has a point spaced equidistantly from opposite axial ends, if viewed along the axis of rotation, and lying in the plane of symmetry.

Thus, the solid body continuously intercepts the beam of light and is shaped so that as it rotates each subsequent segment of the light beam is either greater or lesser than a previous segment, thereby achieving monotonically variable distribution throughout the greatest possible range of light-to-dark. This is achieved by a succession of axial planes each having a respective pair of opposite flanks outwardly diverging from the plane of symmetry and followed by another succession of axial planes, each having opposite flanks inwardly converging toward the plane of symmetry. Thus, an angle formed between the opposite flanks of each subsequent axial plane gradually increases, and then, upon reaching a 180 angle, gradually decreases along a cam surface of the dimmer. For the exception of one axial plane, each plane, thus, has either a nadir or an apex depending on whether the flanks diverge or converge with respect to the plane of symmetry.

The lesser angular distance between subsequent nadirs and apexes along the plane of symmetry the smoother an arc described by the plane of symmetry is, thereby gradually approaching Bezier transition between nadirs and apexes. As a consequence, the greater a number of subsequent radial planes is the more monotonic the distribution of light output is.

In accordance with a narrow aspect of the invention, the dimmer has a plurality of individual vanes. Each of the vanes has an outer side including a pair of flanks either converging toward the plane of symmetry or diverging therefrom to form a succession of apexes and nadirs.

Each embodiment, thus, has formations defining a configuration of a light transmission region depending upon an angular position of the rotation axis.

Thus, as the dimmer rotates, a path of light is intercepted by a series of smoothly shaped solid body or angularly spaced apart vanes defining a series of dimmed regions of an entrance plane of a fiberoptic conductor and producing substantially monotonic distribution of light output.

According to another feature of the invention, the dimming assembly may be provided with a device providing controllable rotation of a shaft and having a memory storing a variety of parameters which corresponds to positions of the axis of rotation wherein selective areas to be examined are best illuminated. If a surgeon decides that a surgical area has been best illuminated with one of the previously used segments or vanes, she can automatically rotate the dimmer until this desirable radial plane intercepts a light beam.

It is therefore an object of the invention to provide an endoscopic device including a dimming assembly which has minimal variations in light-distribution and spectral characteristics in response to changes of the luminous flux of illuminating light which enters a fiberoptic conductor.

Yet another object of the invention is to provide a rotatable dimming assembly having a solid cam body with a succession of adjacent segments which extend in a plane spaced radially asymmetrically from a rotation axis to controllably block the luminous flux of illuminating light without producing a ringing phenomenon.

Yet another object of the invention is to provide an endoscopic device with a dimming assembly having an array of differently shaped vanes which rotate about an axis extending transversely to an optical beam to controllably block the luminous flux of illuminating light without producing a ringing phenomenon.

It is still another object of the invention to provide an endoscopic device with a dimming assembly having a large dynamic range of adjustment of an output beam of light exiting a fiberoptic conductor.

A further object of the invention is to provide an endoscopic device with a mechanical dimming assembly that has a simple, reliable mechanism, which practically needs no maintenance.

BRIEF DESCRIPTION OF THE DRAWINGS

The above and other objects, features and advantages will become more readily apparent from the following detailed description accompanied by the drawings, in which:

FIGS. 1a–1e are diagrammatic views showing different light patterns produced by various dimming schemes of the known prior art.

FIGS. 5a–5g are diagrammatic views showing gradual blockage of a light beam from a source of light to en entrance plane of a fiberoptic conductor and an output light beam exiting the fiberoptic conductor in response to this blockage.

DETAILED DESCRIPTION OF THE DRAWINGS

Figure 2:
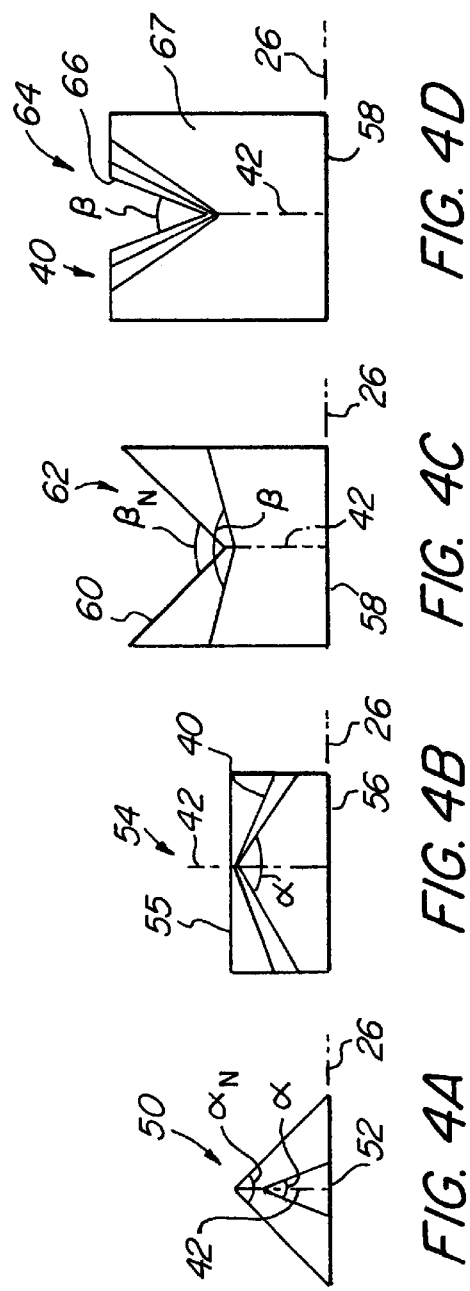
FIG. 2 is an axial cross section of a dimming assembly according to the invention.

Referring to FIGS. 2–5, an optical system including a dimming assembly 20, which smoothly varies intensity of light in accordance with the invention, is shown. Referring to FIG. 2, the dimming assembly 20 includes a light source 22 which typically is used with a xenon bulb intended to be operated at its full output during the entire time of a surgery. Dimming its light is accomplished by downstream blockage or diversion. Specifically, a three-dimensional dimmer 24 has a body with a cam surface 18 shaped and sized to controllably reduce the amount of light from the light source and to selectively illuminate surgical areas while rotating the dimmer about a rotation axis 26. This rotation axis extends transversely to an optical axis 28 of a light beam 30 and, preferably, lies on its boundary so as not block the light beam in a certain angular position of the dimmer, as will be explained hereinafter. Preferably, the axes 26 and 28 extend in substantially parallel planes but perpendicular to each other.

The light beam 30 is conducted to a lens assembly 32 which upon condensing this beam focuses it toward an entrance plane 34 of a fiberoptic conductor 36 emitting an output beam which is rotationally faithful to the light beam 30. The cam surface 18 occludes the light beam converging on the fiberoptic conductor 36 which produces exit patterns whose brightness does not vary substantially across it, thereby substantially uniformly illuminating a region under investigation.

According to one aspect of the invention shown in FIG. 2, the dimmer 24 is a solid three-dimensional body 100 which is opaque and is made of a heat-resistant metal. The body 100 is formed with a cam surface 18 which has a plane of symmetry 42 extending transversely to and radially outwardly from the rotation axis 26 of a shaft 38. The cam surface 18 extending substantially over a 180° rotational range bridges opposite sides 16 of the body 100 and has opposite outer edges 6 partly defining these sides 16. The cam surface is shaped so that as it rotates about the rotation axis 26, the light beam 30 is intercepted to have a series of differently shaped regions (FIG. 5) masked on the two-dimensional entrance plane 34 of the fiberoptic conductor 36.

Particularly, the cam surface 18 has an array of wedge-shaped axial planes 14, each sub-divided in two cam-surface regions 14a and 14b meeting one another in the plane of symmetry 42 to form a continuous succession of ridges 12 and troughs 10 along this plane of symmetry. Thus, a first series of planes 14 has a progressively increasing apex angle $\lambda_1 - \lambda_n$ varying from an acute angle to a substantially 180° angle. Obviously, in order to form a continuously increasing apex angle, the regions 14a, 14b converge outwardly from the rotation axis 26 toward the plane of symmetry 42 to have the ridges 12 extending along the plane of symmetry 42.

A second series of the regions 14a, 14b converging inwardly toward the plane of symmetry 24 at a gradually decreasing nadir angle $\beta$ to form a succession of troughs 10. As a consequence, the nadir angle $\beta$ decreases from an obtuse angle to an acute one. Preferably, the smallest nadir angle $\beta_n$ is substantially equal to the smallest nadir angle so that the smallest nadir angle $\lambda_1$.

Thus, the three-dimensional body 100 has a cam surface extending substantially over a 180 angle and having a series of wedge-shaped radial planes 14, each of which has a pair of regions 14a, 14b forming either the ridge 12 or trough 10 that extends along the plane of symmetry.

To have minimal variations in light-distribution and spectral characteristics in response to changes of the flux of illuminating light intercepted by a series of planes, an angle $\mu$ between adjacent axial planes 14 has to be so selected that a succession of troughs and ridges forms a continuous curve. This is achieved by a solid three-dimensional body 100' having a plurality of radial planes 14' that substantially exceeds a number of the planes 14 of the embodiment shown in FIG. 3A. By increasing a number of planes 14', it is possible to have two curved halves 17' and 17" of a cam surface 19, which are symmetrical with respect to a curved plane of symmetry 42'. Clearly, by increasing the number of planes, it is possible to obtain a smooth transition between troughs and ridges. Thus, each angular displacement of the body 100' about a rotation axis 26' finely changes an intensity of light beam by gradually increasing or decreasing a sector of the light beam which intercepted by each successive radial plane, as better illustrated in FIG. 5.

Figure 3A:
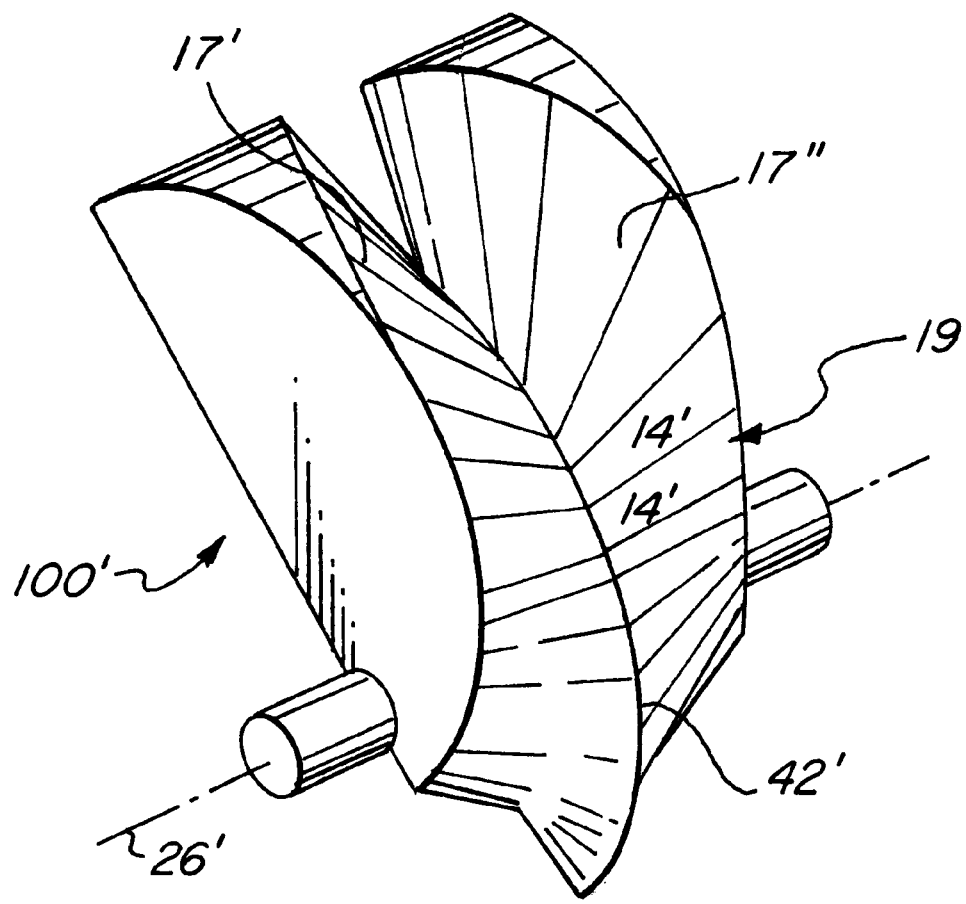
FIG. 3A is an isometric view of the dimming assembly shown in FIG. 2.
Figure 3C:
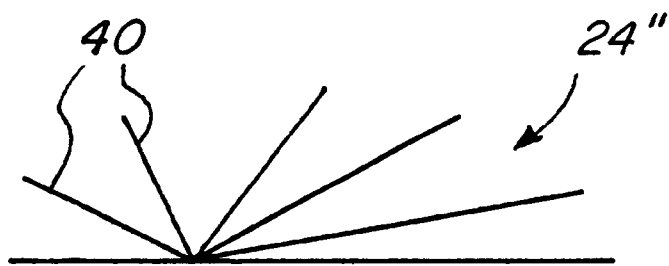
FIG. 3C is a side view of another embodiment of the dimming assembly having a plurality of angularly spaced vanes.
Figure 3B:
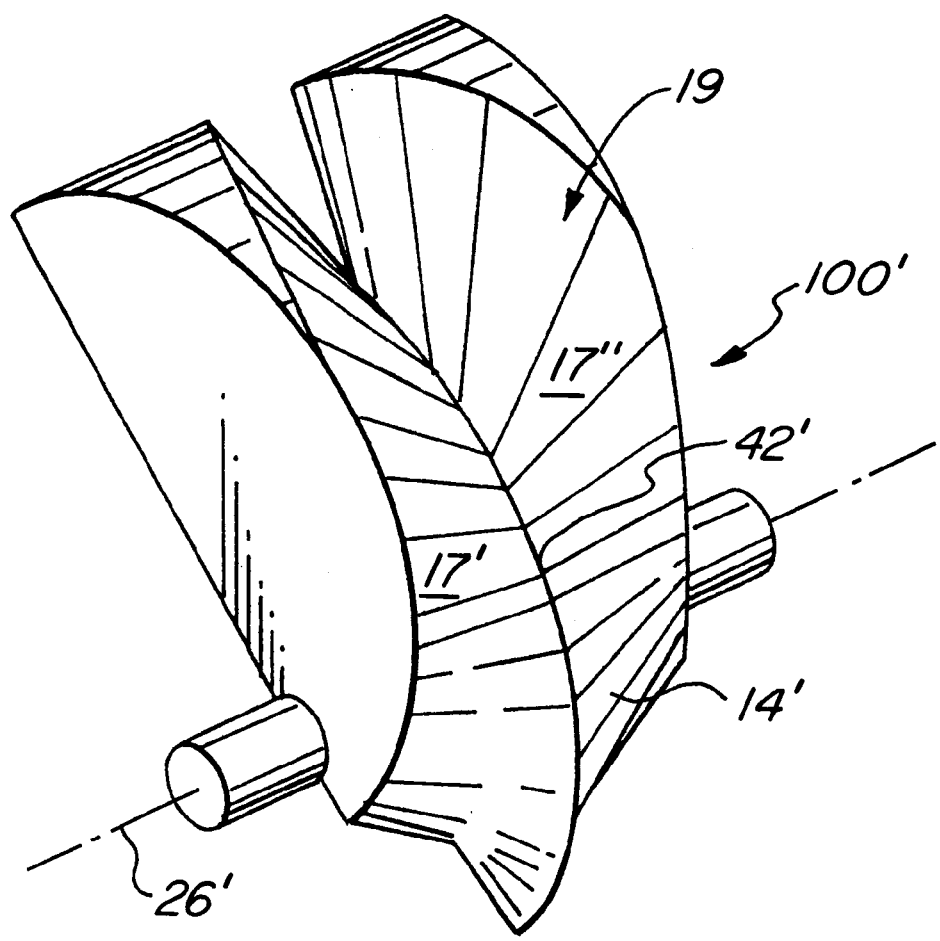
FIG. 3B is an isometric view of the dimming assembly similar to the one shown in FIG. 3A but having a number of radial planes greatly increased in comparison with the dimming assembly of FIG. 3A.

According to another embodiment shown in FIG. 3C, the dimmer 24" has an array of separate wedge-shaped vanes 40 which are spaced angularly apart. Although this embodiment can be relatively easily manufactured, an adjustment of luminous flux would not be as fine as the one made by the dimmer, which is shown in FIG. 3A, and, in particular, by the dimmer which is illustrated FIG. 3B.

Common to all of the embodiments is a combination of cross-sections of the wedge-shaped radial planes (FIGS. 3A and 3B) and the vanes (FIG. 3C) which generally includes four groups. Although the following description refers to the embodiment of the dimmer having a plurality of discreet vanes, as shown in FIG. 3C, it is understood that this description is invariably the same with respect to the embodiments illustrated in FIGS. 3A and 3B.

Figures 4A, 4B, 4C, 4D:
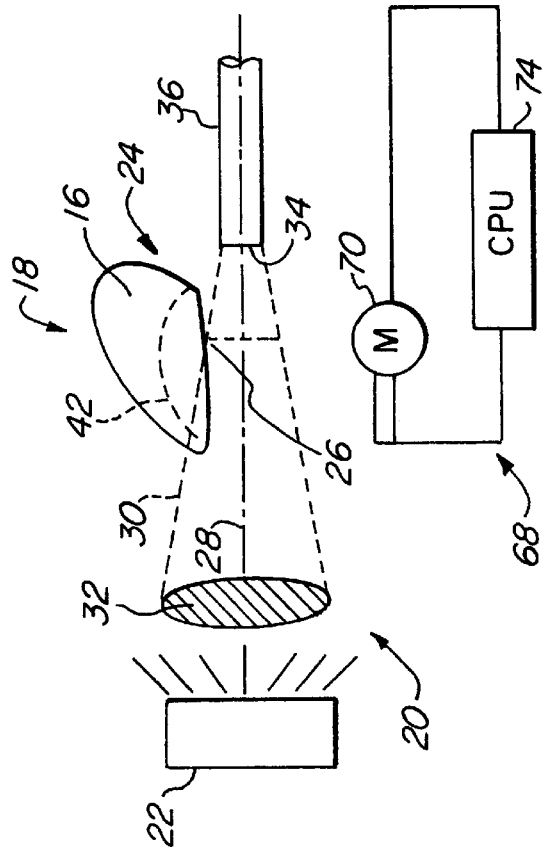
FIGS. 4a–4d are cross-sectional views of differently shaped vanes taken along a plane of symmetry of the dimming assembly.

Thus, as shown in FIG. 4a, a first group of vanes 40 includes a plurality of triangular vanes 50, each having an apex which terminates at the plane of symmetry 42. An apex angle λ progressively increases to an apex angle $λ_n$ so as to preferably have a length of a base side 52 of the largest triangular vane 50, which is mounted to the shaft, equal to base lines 56, 58 of a following second group of vanes 50. Also, a distance of an apex of each subsequent triangular vane from the rotation axis 26 is greater than such distance of the previous one.

Each of the vanes of the second group of 54 has a pentagonal cross-section, as shown in FIG. 4b. Similarly to the previously described group of triangular vanes, an apex angle of each successive pentagon is greater than an angle of the previous one. This angle gradually increases to a substantially 180° angle converting, thus, a pentagonal cross-section to a rectangular one whose single outer line 55 extends substantially parallel to the shaft axis 26.

The next two groups include polygons whose outer lines instead of having an apex are formed with a cutout defining a gradually decreasing nadir angle , as shown in FIGS. 4c and 4d.

Specifically, each pentagonal cross-section 62, as shown in FIG. 4c, is formed with inwardly converging sides 60 forming a progressively decreasing nadir angle from an obtuse angle β to an acute angle $β_n$.

FIG. 4d shows the last group 67 having an array of vanes 66, each having an octagonal cross-section with a nadir angle β. Clearly, this angle decreases further until it substantially equals to the smallest apex angle of the smallest triangular vane of the first group.

The largest radial distance at which the opposite sides 6 of the dimmer 24 extend from the axis of rotation axis 26 preferably is so selected that the sides cover a distance between boundaries of the light beam 30. Thus, the dimmer is so sized that that rotation of the axis 26 at a 360° angle successively brings the dimmer from a position, wherein the largest vane or radial plane extends between the boundaries of the light beam, to a position, wherein the light beam is not intercepted. A plurality of intermediate positions are determined by smoothly varying apex λ and nadir β angles upon rotation of the dimmer about the rotation axis 26.

Note that the shapes described here are given only as an example and many other variations and configurations are possible as long as abrupt changes are avoided to produce a sensibly uniform illumination pattern. Thus, any combination of shapes and sizes of the array of vanes 40 or radial planes 14 sequentially introduced into the beam 30 to obtain a smooth variation of intensity of light as described above falls within the scope of this invention.

Also, note that the largest radial distance may vary either not reaching a distance between boundaries of the light beam or exceeding it. This distance may depend on particular needs of a surgeon, target areas, light intensity requirements and etc. In the preferred embodiment, the plane of symmetry is tangential with respect to the optical axis 28, thus leaving the light beam 30 unblocked substantially over a 180° angle.

Thus, the dimmer 24, as shown in FIGS. 3A–3B and 4a–4d can be characterized as bilaterally symmetrical, if it is viewed along the optical axis 28, and rotationally asymmetrical, as seen along the rotation axis 26.

Referring to FIGS. $5_1$–$5_{28}$, an adjustment sequence can be easily understood by starting, for an instance, with FIG. $5_1$ which shows practically the full light beam 30. Depending on a direction of rotation, an apex 78 progressively approaches the optical axis 28 and finally reaches it, as is shown in FIG. $5_9$. Further displacement of the shaft about the rotation axis 26 results in a gradual coverage of the upper half of the beam 30, as shown in FIGS. $5_2$–$5_{16}$. Generally, as shown in theses figures, a cross-section of the dimmed region during displacement of first two groups of vanes 50, 54 or radial planes 14 in a rotational direction 38 is defined by two converging flanks 80, 82 or regions 14a,14b of respective radial planes 14. With gradual increase of the apex angle λ, a dimmed area of the beam approaches a semicircular shape, finally reaching it, as shown in FIG. $5_{17}$.

Upon further displacement of the shaft, the dimmed area gradually increases going through stages characterized by a smooth contour without apexes, as shown in FIGS. $5_{18}$–$5_{22}$. A cross-section of the dimmed region of the beam 30 is characterized by diverging opposite flanks 86, 88. Finally, only a small central region 84 defined by the dove-tail recess of the last vane 64 (FIG. 4d) or respective regions $14_n$ (FIG. 3) remains illuminated by 50% of the light of the beam, whereas outer sides 90–92 (FIG. $5_{22}$) extend tangentially to the lower boundary of the beam. Thus, as seen in FIGS. $5_1$–$5_{28}$, this invention produces an output beam of sensibly constant intensity across it, without a bright center and dark outer regions. Further, no upper or lower limits are imposed on transmission, because, with minor modifications of the cross-sections of the cam regions and the vanes, the beam can be entirely blocked and can have all settings between zero and full illumination. As a consequence, intensity of illumination at the entrance plane of the fiberoptic conductor and the luminous density at the exit plane thereof is easily controlled.

Figure 6:
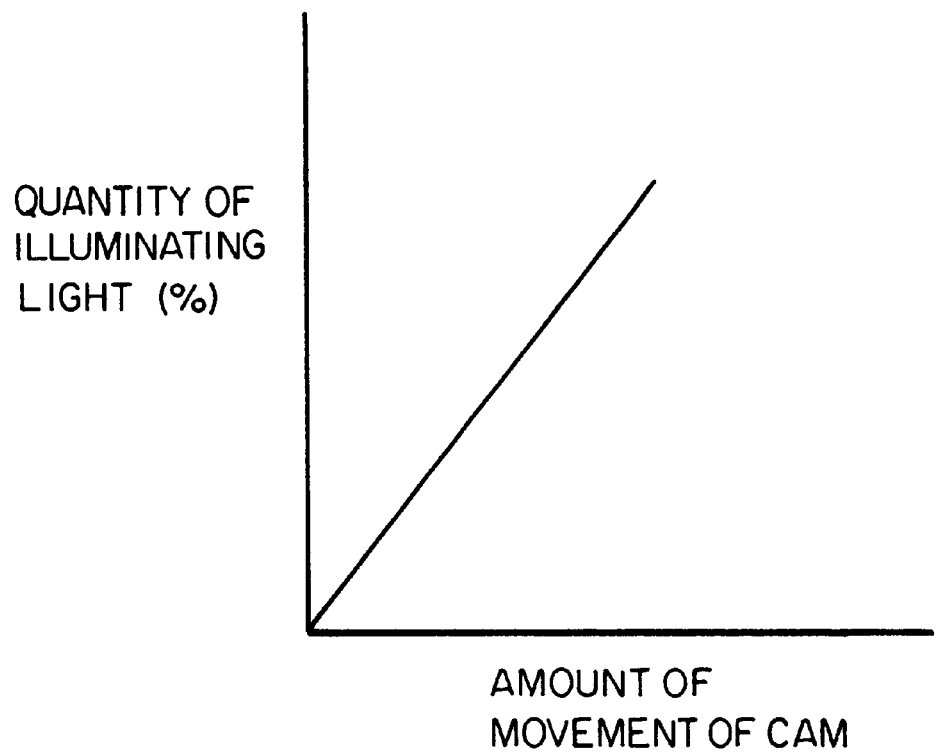
FIG. 6 is a graph illustrating a change of the quantity of illuminating light with the amount of displacement of a dimmer assembly shown in FIGS. 3 and 4

As shown in FIG. 6, a change of the quantity of illuminating output light linearly changes in response to the amount of movement of the tree-dimensional cam 100 or a plurality of wanes 40. As a consequence, there is not sudden change in the in the quantity of light and the ringing phenomenon is practically eradicated. Thus, even if the luminous flux entering the fiberoptic conductor 36 is changed to a considerable extent, no distinct changes occur in the light-distribution and spectral characteristics of light emanating from the light sources 22.

The dimming assembly can be manually and automatically controlled by a controller 68. If the assembly is automatically controlled, a microprocessor control unit 74 (FIG. 2), which is well known in the art, allows the light intensity to be automatically set by a camera. Still another possibility of electronically controlling the assembly may be use of a stepper motor 70 having a number of steps of which is easily counted and stored in database. As a consequence, when a surgeon, after having tried several different vanes, determines that one of the previously used vanes or segments is most suitable, the dimmer will be easily rotated in a desirable angular position.

Various modifications of the disclosed embodiment of the invention will be readily apparent to those skilled in the art, and all changes and modifications which could be possibly made to the embodiments of this invention fall within the scope of the following claims.

What is claimed is:

1. A dimmer comprising:
   a source of light emitting a light beam extending along a path; and
   a light shaper comprising a succession of opaque regions and rotatable about an axis of rotation which is transverse to the path, the opaque regions being successively insertable into the path and having outlines of different geometric shapes defining a configuration of a light-transmission region depending upon the angular position of the light shaper about the rotation axis;

wherein, the succession of opaque regions includes a first group of consecutive axial planes, each of the axial planes having a respective pair of regions converging toward one another to form an apex angle therebetween.

2. The dimmer defined in claim 1 wherein the light shaper is a solid body having a plane of symmetry extending perpendicular to the axis of rotation.

3. The dimmer defined in claim 2 wherein the succession of opaque regions includes a second group of consecutive axial planes, each having a respective pair of regions diverging from the plane of symmetry to form a nadir angle therebetween on the plane of symmetry.

4. The dimmer defined in claim 1 wherein the apex angle continuously varies between an acute angle and an obtuse angle as the dimmer rotates.

5. The dimmer defined in claim 3 wherein the nadir angle continuously decreases between an obtuse angle and an acute angle.

6. The dimmer defined in claim 2 wherein the plane of symmetry extends along a 180° path and is an arcuate curve.

7. The dimmer defined in claim 2 wherein the plane of symmetry is defined by a plurality of adjacent linear troughs and ridges formed by respective axial planes extending along substantially a 180° path.

8. The dimmer defined in claim 1 wherein the axis of rotation extends perpendicular to the path, the path and the axis of rotation lying in parallel planes.

9. The dimmer defined in claim 1 wherein the succession of regions is a plurality of separate vanes spaced angularly apart and extending radially outwardly from the axis of rotation.

10. The dimmer device defined in claim 9 wherein each subsequent vane introduced into the path extends progressively father away from the axis of rotation until a largest vane bridges boundaries of the path.

11. The dimmer defined in claim 9 wherein the plurality of vanes includes a number of groups.

12. The dimmer defined in claim 11 wherein one of the groups includes a plurality of triangular vanes, each having an apex angle progressively increasing from the smallest triangular vane to the largest one.

13. The dimmer defined in claim 12 wherein the one group is followed by a second group including a series of vanes having pentagonal cross-sections; each being formed with an apex angle the smallest of which is greater than the apex angle of the largest triangular vane.

14. The dimmer defined in claim 13, wherein the apex angle of the largest vane of the second group being substantially equal to a 180° so as the largest vane of the second group substantially has a rectangular cross-section.

15. The dimmer defined in claim 13, wherein the second group of opaque vanes is followed by a third group including a series of vanes having a pentagonal cross-section, each having a pair of outer sides which converge inwardly toward one another to form a nadir angle, the nadir angle progressively decreasing from an obtuse angle to an acute one.

16. The dimmer defined in claim 15, wherein the third group of opaque vanes is followed by a fourth group including a series of vanes, each having an octagonal cross-section formed with an outer sides converging inwardly toward one another to form a nadir angle progressively decreasing from the one which is smaller than the acute angle of the largest vane of the third group until the nadir angle of the fourth group substantially equals to the smallest apex angle of the smallest triangular vane.

17. An endoscope assembly comprising:
   a source of light emitting a light beam propagating along a path having an optical axis;
   a fiberoptic conductor downstream from the source of light and having an entrance plane;
   a dimming assembly between the source of light and the entrance plane of the optical fiber and comprising an array of opaque regions rotatable about an axis of rotation which extends perpendicular to the path, the opaque regions being successively insertable into the path and having outlines of different geometric shapes defining a configuration of a transmission region depending upon an angular position of the dimming assembly about the axis of rotation;
   wherein, the succession of regions is a Plurality of vanes spaced apart at a uniform angle.

18. The endoscopic device defined in claim 17 wherein the axis of rotation extends parallel to a plane of the optical axis, the endoscopic device further comprising a rotatable shaft extending along the axis of rotation and supporting the array of vanes.

19. The endoscope defined in claim 17 wherein the plurality array of vanes extends along a rotational range defining a plane of symmetry extending along a path which is less than 360°.

20. The endoscopic device defined in claim 17 wherein the plurality of vanes includes groups of differently shaped vanes selected from the group consisting of triangular, pentagonal and octagonal cross-sections.

21. The endoscopic device defined in claim 17 wherein each subsequent region is adjacent to a previous one, thereby forming a solid cam body.

22. The endoscopic device defined in claim 21 wherein each region has two sub-regions forming a succession of ridges and troughs which extend along a plane of symmetry of the solid cam body extending transversely to the axis of rotation.

23. The endoscopic device defined in claim 22 wherein each of the ridges has an apex angle varying from an acute angle to a substantially 180°, and each of the troughs having a nadir angle following the group of the apex angles and varying from an obtuse angle to an acute angle.

* * * * *